United States Patent
Yamada

(10) Patent No.: US 6,587,594 B1
(45) Date of Patent: Jul. 1, 2003

(54) MOIRE ELIMINATING FILTER AND IMAGE PROCESSING METHOD AND APPARATUS USING THE FILTER

(75) Inventor: Masahiko Yamada, Kanagawa-ken (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/329,218

(22) Filed: Jun. 10, 1999

(30) Foreign Application Priority Data

Jun. 12, 1998 (JP) .......................................... 10/164737

(51) Int. Cl.$^7$ ............................. G06K 9/40; G06K 9/00; G06K 15/00; H04N 1/46
(52) U.S. Cl. ...................... 382/260; 382/132; 358/3.26; 358/533
(58) Field of Search ................................ 382/132, 276, 382/260; 358/3.26, 533, 1.9; 356/605, 618; 250/550

(56) References Cited

U.S. PATENT DOCUMENTS

| | | | |
|---|---|---|---|
| 4,258,264 A | | 3/1981 | Kotera et al. ................ 250/484 |
| 4,276,473 A | | 6/1981 | Kato et al. ................ 250/327.1 |
| 4,315,318 A | | 2/1982 | Kato et al. .................... 364/515 |
| 5,028,784 A | | 7/1991 | Arakawa et al. ......... 250/327.2 |
| 5,351,312 A | * | 9/1994 | Sato et al. .................... 382/252 |
| 5,881,162 A | * | 3/1999 | Ishimitsu .................... 382/132 |
| 6,173,086 B1 | * | 1/2001 | Hara .......................... 382/128 |
| 6,233,060 B1 | * | 5/2001 | Shu et al. ..................... 358/1.9 |
| 2002/0196901 A1 | * | 12/2002 | Inoue .......................... 378/154 |

FOREIGN PATENT DOCUMENTS

| | | | |
|---|---|---|---|
| JP | 55(1980)-12429 | 1/1980 | |
| JP | 55(1980)-116340 | 9/1980 | |
| JP | 55(1980)-163472 | 12/1980 | |
| JP | 56-11395 | 2/1981 | ............ G21K/4/00 |
| JP | 56-164645 | 12/1981 | ............ H04J/1/10 |
| JP | 01-194769 | * 4/1989 | .......... H04N/5/253 |
| JP | 3(1991)-12785 | 3/1991 | |
| JP | 3(1991)-114039 | 3/1991 | |

* cited by examiner

*Primary Examiner*—Kimberly A. Williams
*Assistant Examiner*—Melanie Vida
(74) *Attorney, Agent, or Firm*—Sughrue, Mion, PLLC

(57) ABSTRACT

Stripe patterns caused by grids having different pitches can be reduced when image data obtained by reading images photographed by using the grids are reproduced. A radiation image is read from a stimulable phosphon sheet on which the radiation image has been recorded by photographing using a grid of 3.4 lines/MM. Filtering processing by filtering means is carried out on digital image data obtained by the reading. The coefficients of a filter used in the filtering processing are −1, −1, 4, −3, −14, 0, 43, 68, 43, 0, −14, −3, 4, 1, −1. This filter is to reduce a response of a spacial frequency equal to or more than 3.3 cycles/mm to equal to or less than 5%, preferably to equal to or less than 2%. In processed image data obtained through filtering processing using such a filter, a response of 3.4 cycle/mm or 4.0 cycle/mm frequency corresponding to the grid of 3.4 lines/mm or 4.0 lines/mm is reduced, and an image having a suppressed stripe pattern caused by the grid can be obtained by reproduction of the processed image data.

10 Claims, 7 Drawing Sheets

F I G . 3
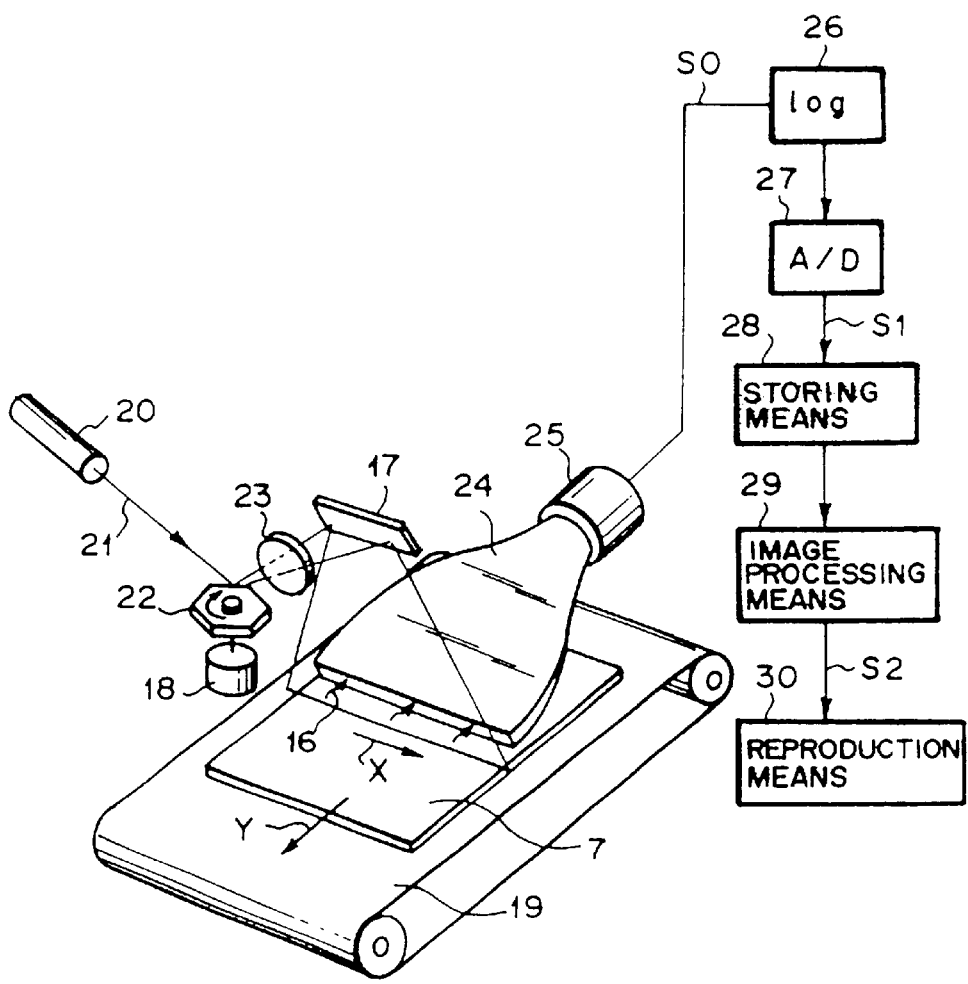

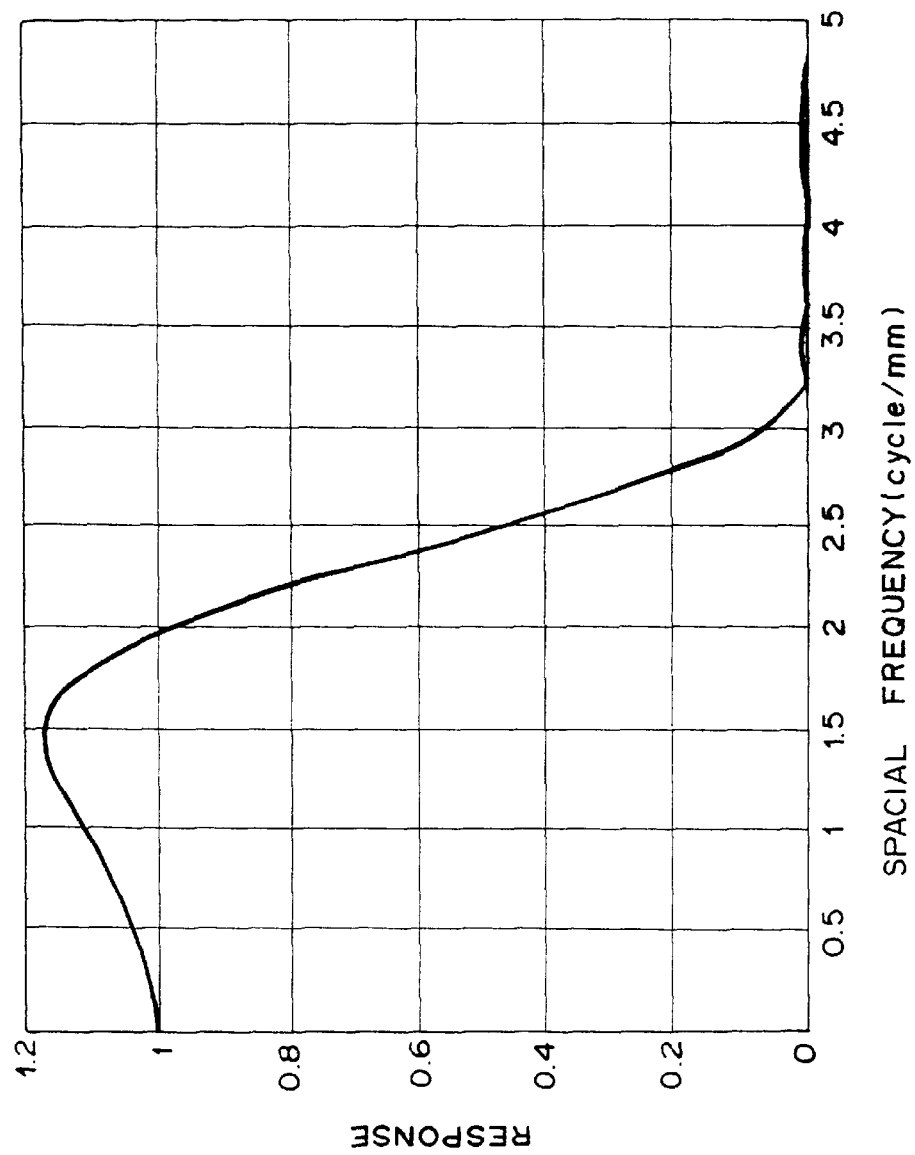
F I G. 5

MOIRE ELIMINATING FILTER AND IMAGE PROCESSING METHOD AND APPARATUS USING THE FILTER

BACKGROUND OF THE INVENTION

1. Field of the Invention

The present invention relates to a moire eliminating filter used in the case where filtering processing for eliminating a grid image is carried out on image data representing a subject image having a stripe pattern (moire) superposed on the image and corresponding to a grid used in photographing, and also to an image processing method and apparatus using the filter.

2. Description of the Related Art

Radiation image recording reproducing systems using stimulable phosphon which emits light, upon exposure to stimulating rays such as visible light, in accordance with radiation energy stored therein originated from a radiation (such as X rays, α rays, β rays, γ rays, electron rays, and ultraviolet rays) having been irradiated thereon have been known (see Japanese Unexamined Patent Publication Nos. 55(1980)-12429, 56(1981)-11395, 55(1980)-163472, 56(1981)-164645, and 55(1980)-116340, for example). A radiation image recording reproducing system records a radiation image of a subject such as a human body on a stimulable phosphon sheet and the sheet is scanned with stimulating rays such as a laser beam in order to cause the sheet to emit light. The emitted light is read photoelectrically by reading means such as a photomultiplier and an image signal is obtained thereby. Based on the image signal, the radiation image of the subject is output by the radiation image recording reproducing system, as a visible image on a recording medium such as a photosensitive material or on a CRT display.

When a radiation image of a subject is recorded on a stimulable phosphon sheet or the like, a grid composed of alternately placed, in a fine pitch such as 4 lines/mm, lead or the like which is not penetrable by radiation and aluminum or wood or the like which is penetrable by radiation is placed between the subject and the sheet in some cases so that radiation scattered by the subject is not irradiated on the sheet. Since radiation scattered by a subject is rarely irradiated on a sheet when the grid is used at the time of photographing, contrast of a radiation image of the subject can be improved. However, a fine stripe pattern (moire) corresponding to the grid is also recorded on the sheet together with the subject image, and a reproduced image becomes indistinct.

For this reason, a method of obtaining a distinct image with reduced moire by carrying out Fourier-transform followed by inverse Fourier transform on image data to eliminate frequency data corresponding to a grid pattern, or by carrying out filtering processing to eliminate a spacial frequency component corresponding to a grid pattern has been proposed (Japanese Unexamined Patent Publication Nos. 3(1991)-12785 and 3(1991)-114039, for example). In the case where a grid pitch is 4.0 lines/mm for example, a stripe pattern appears around a spacial frequency band of 4.0 cycles/mm. Therefore, in the above method, the stripe pattern is eliminated by applying filtering processing using a filter to eliminate or reduce a response of this frequency band.

The grid pitch described above is not limited to 4.0 lines/mm, and 3.4 lines/mm is used in some cases. When such a grid of 3.4 lines/mm is used, a stripe pattern should appear in a spacial frequency band of 3.4 cycles/mm. However, since the filter used in Japanese Unexamined Patent Publication No. 3(1991)-12785 and the like is to eliminate or reduce a response of only a specific spacial frequency, a stripe pattern caused by a grid of a different pitch cannot be eliminated thereby. As a result, a reproduced image has moire and is not distinct. For example, in the case where a stripe pattern is eliminated by using a filter having a characteristic shown in FIG. 7 while an image is being reduced by ½, a response of a spacial frequency of 4.0 cycles/mm caused by a grid having a pitch of 4.0 lines/mm can be reduced. On the other hand, a response of a spacial frequency of 3.4 cycles/mm caused by a grid having a pitch of 3.4 lines/mm cannot be reduced. As a result, a stripe pattern caused by the 3.4 line/mm pitch grid appears in a reproduced image. Furthermore, in the case where a stripe pattern is eliminated by using a filter having a characteristic shown in FIG. 8 while an image is being reduced to ⅔, the response of the spacial frequency of 4.0 cycles/mm caused by the grid having the pitch of 4.0 lines/mm can be reduced. On the other hand, the response of the spacial frequency of 3.4 cycles/mm caused by the grid having the pitch of 3.4 lines/mm cannot be reduced.

In this case, filtering processing using a filter for eliminating or reducing a response of a spacial frequency corresponding to a pitch of a grid to be used is possible. However, at the time of filtering processing, it is difficult to identify what pitch the grid used at the time of photographing has. Therefore, filters of a plurality of kinds are necessary, and memory space for storing the filters becomes large.

SUMMARY OF THE INVENTION

The present invention has been conceived based on consideration of the above problems. An object of the present invention is to provide a moire eliminating filter and an image processing method and apparatus using the filter for carrying out filtering processing on image data in order to cause a stripe pattern generated by a grid to become inconspicuous even when a grid pitch varies.

A moire eliminating filter of the present invention reduces a response of a spacial frequency component of a stripe pattern in image data obtained by reading an image including the stripe pattern corresponding to a grid of n line/mm pitch used at the time of photographing the image, and the filter reduces the response of a spacial frequency component equal to or more than 97% of the spacial frequency component corresponding to the grid pitch to equal to or less than 5%, preferably to equal to or less than 2%.

As the grid pitch, 3.4 lines/mm, 4.0 lines/mm, and the like are used, and moire caused by these grids appears in spacial frequencies of 3.4 cycles/mm and 4.0 cycles/mm, for example. However, since the grid may not have been set parallel to a sheet or attached to a sheet incompletely, the spacial frequency of moire can shift slightly to the lower frequency side. Therefore, in the present invention, the spacial frequency component corresponding to the grid pitch is shifted to the lower frequency side by approximately 3%, and a response of a spacial frequency component (for example, 3.3 cycles/mm) of equal to or more than 97% of the spacial frequency component corresponding to moire (for example, 3.4 cycles/mm) is reduced to equal to or less than 5%.

Meanwhile, in the case where frequency data of the spacial frequency corresponding to moire are filtered by using Fourier transform, the response of the spacial frequency can be 0. However, this operation is time consuming.

In order to carry out filtering processing quickly, filtering processing in real space, not in frequency space, is used. However, in the real space, the degree of a real space filter is finite and a response of a specific spacial frequency cannot be 0. Therefore, in the present invention, the response of spacial frequency components of equal to or more than 97% of the spacial frequency component corresponding to moire is reduced to equal to or less than 5%, preferably to equal to or less than 2%.

The image processing method of the present invention carries out filtering processing by using the moire eliminating filter of the present invention.

An image processing apparatus of the present invention comprises filtering means for carrying out filtering processing using the moire eliminating filter of the present invention.

According to the moire eliminating filter of the present invention, since the response of the spacial frequency components of equal to or more than 97% of the spacial frequency component corresponding to a grid pitch is reduced to equal to or less than 5%, a stripe pattern caused by a grid of any pitch can be reduced after image data have been filtering-processed. Therefore, by subjecting image data to filtering processing using the filter of the present invention, a reproduced image with an inconspicuous stripe pattern can be obtained.

BRIEF DESCRIPTION OF THE DRAWINGS

FIG. 3 is an illustration showing an example of a radiation image reading apparatus;

FIG. 5 is a graph showing a characteristic of a filter F;

DESCRIPTION OF THE PREFERRED EMBODIMENT

Hereinafter, an embodiment of the present invention will be explained with reference to the accompanying drawings.

Figure 1:
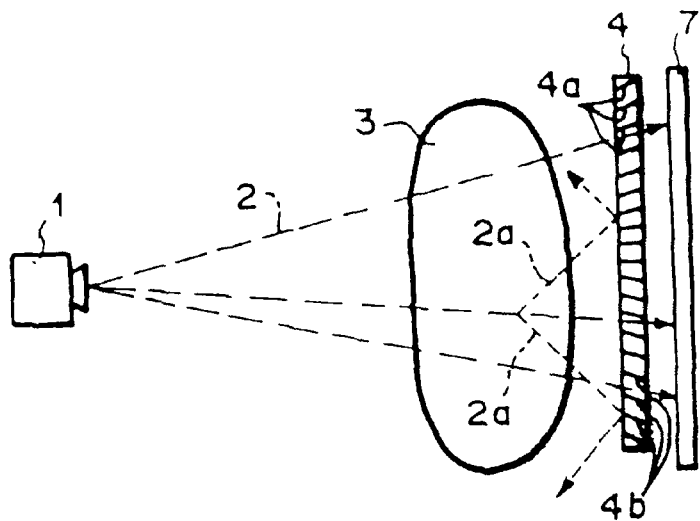
FIG. 1 is an illustration showing an example of a radiation image photographing apparatus.

FIG. 1 is an illustration showing an outline of a radiation image photographing apparatus. The stimulable phosphon sheet described above is used as a recording sheet in this embodiment.

Radiation 2 emitted from a radiation source 1 is irradiated on a stimulable phosphon sheet 7 through a subject 3 and a grid 4. The grid 4 is composed of lead 4a and aluminum 4b alternately placed on a pitch of 3.4 lines/mm. The radiation 2 is intercepted by the lead 4a but passes through the aluminum 4b and is irradiated on the sheet 7. Therefore, a stripe pattern of 3.4 lines/mm is recorded on the sheet 7 together with a radiation image of the subject 3. Radiation 2a scattered within the subject 3 obliquely enters the grid 4. Therefore, the radiation 2a is shielded or reflected by the grid 4, and cannot enter the sheet 7. Therefore, the radiation image which is sharp and has a reduced effect of the scattered radiation is recorded on the sheet 7.

Figure 2:
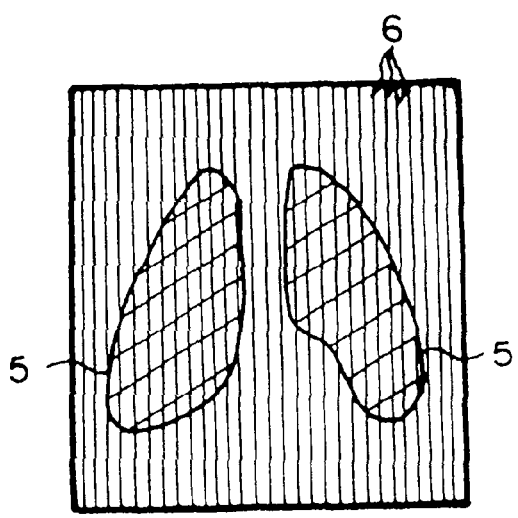
FIG. 2 is an illustration showing a radiation image obtained by photographing using a grid.

FIG. 2 shows an example of the radiation image of the subject (diagonally hatched areas in FIG. 2) superposed by a stripe pattern (stripe pattern in FIG. 2) caused by the grid used at the time of photographing. As shown in FIG. 2, the radiation image which is a composite of a subject image 5 and a stripe pattern 6 is recorded on the stimulable phosphon sheet 7.

FIG. 3 is an illustration showing a radiation image reading apparatus.

The stimulable phosphon sheet 7 recording the radiation image is set at a predetermined position of the radiation image reading apparatus and conveyed (vertical-scanned) in a direction shown by an arrow Y by sheet conveying means 19 such as endless belts driven by driving means which is not shown in FIG. 3. Meanwhile, a light beam 21 emitted from a laser beam source 20 is reflected and deflected by a rotational polygon mirror 22 rotating at high speed in a direction shown by an arrow by being driven by a motor 18. The light beam 21 passes a focusing lens such as an fθ lens and is deflected by a mirror 17 to enter the sheet 7. The light beam 21 main-scans the sheet 7 in a direction shown by an arrow X approximately orthogonal to the vertical scan direction (the direction shown by the arrow Y). At this time, the pitch of the main scan here is assumed to be 10 lines/mm. A portion of the sheet 7 whereon the light beam 21 is irradiated emits light 16 whose amount is in accordance with stored radiation image information, and the emitted light 16 is directed by a light guide 24. The light 16 is then photo-electrically detected by a photomultiplier (photomultiplier tube) 25. The emitted light 16 representing the radiation image is converted into an electrical signal by the photomultiplier 25.

An analog signal S0 output from the photomultiplier 25 includes information of 3.4 cycle/mm spacial frequency band (information of the stripe pattern 6 shown in FIG. 2) lower than fss=5.0 cycles/mm which is the highest spacial frequency (Nyquist frequency) among spacial frequency bands necessary for reproduction of a preferable visible image of the radiation image. The information of the stripe pattern is one of the reasons causing the visible image to be indistinct and needs to be eliminated.

After the analog signal S0 is logarithmically amplified by an logarithmic amplifier 26, the signal S0 is digitized by an A/D converter 27 by being sampled at a predetermined sampling interval. Digital image data S1 are obtained in this manner. The image data S1 are temporarily stored in storing means 28 and transferred to an image processing apparatus 29.

Figure 4:
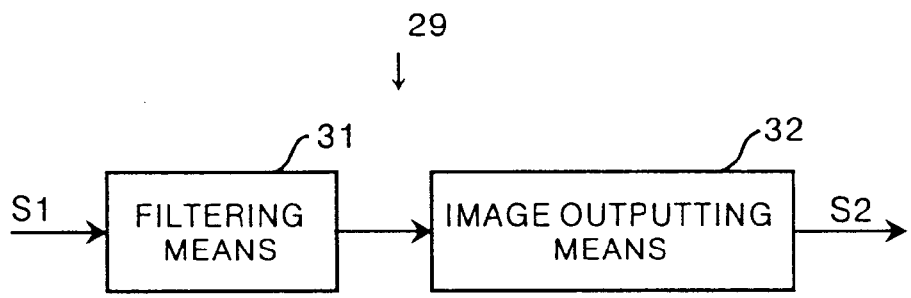
FIG. 4 is a schematic block diagram showing a configuration of an image processing apparatus.

FIG. 4 shows an outline configuration of the image processing apparatus 29 in the form of a block diagram. As shown in FIG. 4, the image processing apparatus 29 comprises filtering means 31 for carrying out filtering processing on the image data S1 to obtain processed image data S2 and image outputting means 32 for outputting the processed image data S2 to reproduction means 30.

Filter coefficients of a filter F used by the filtering means 31 are shown below. The filter has 15 taps (that is, the filter is a 15-degree filter). −1, −1, 4, −3, −14, 0, 43, 68, 43, 0, −14, −3, 4, 1, −1

A characteristic of this filter F is shown in FIG. 5. As shown in FIG. 5, the filter F is for reducing a response of a spacial frequency of equal to or more than 3.3 cycles/mm to equal to or less than 5%.

Sequential filtering processing using the filter F is carried out by the image processing apparatus 29, as will be described below, for example. The filtering processing using the filter F is carried out in the main scan direction on the image data Si corresponding to up to line 14 of the vertical scan. The filtered data are stored in a memory (not shown) in the image processing apparatus 29. After the filtering processing is carried out on image data corresponding to line 15 of the vertical scan, filtering processing using the filter F is carried out in the vertical scan direction on the image data corresponding to line 15 of the vertical scan together with the data corresponding to the 14 lines stored in the memory. The data corresponding to the line processed earliest are erased and the filtering processing is carried out in the main scan direction on data corresponding to a new subsequent line. The filtering processing is then carried out again in the vertical scan direction on the data corresponding to the new 15 lines. By repeating this procedure, the processed image data S2 are obtained. The processed image data S2 are input to the reproduction means 30 by the image outputting means 32, and reproduced as a visible image thereby.

In the processed image data S2 obtained as has been described above, a response of the spacial frequency of equal to or more than 3.3 cycles/mm has been reduced to equal to or less than 5%. Therefore, even when the grid of 3.4 lines/mm or 4.0 lines/mm has been used at the time of photographing, a stripe pattern caused by the grid to appear in a spacial frequency band of 3.4 cycles/mm or 4.0 cycles/mm can be reduced. As a result, a high quality reproduced image without a stripe pattern caused by the grid can be obtained by the reproduction means 30 through reproduction of the processed image data S2.

In the case where the reproduced image is reduced to ½, the stripe pattern caused by the grid can also be reduced by using a filter the same as the filter F. In this case, the filtering processing using the filter F is carried out on each pixel or on each line. The response of the spacial frequency of equal to or more than 3.3 cycles/mm can also be reduced in this case, and a stripe pattern to appear in the spacial frequency band of 3.4 cycles/mm or 4.0 cycles/mm can be suppressed.

Figure 6:
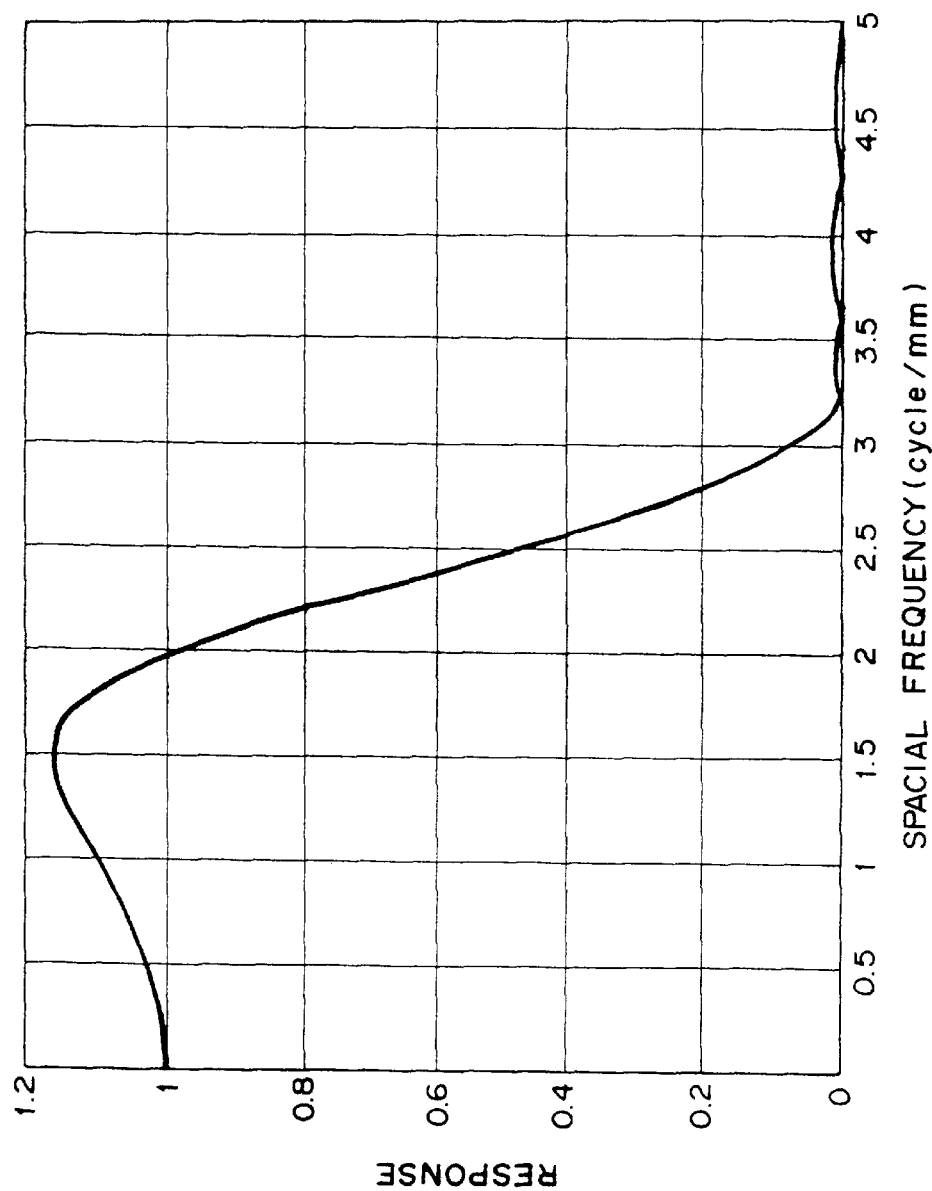
FIG. 6 is a graph showing a characteristic of a filter F1.
Figure 7:
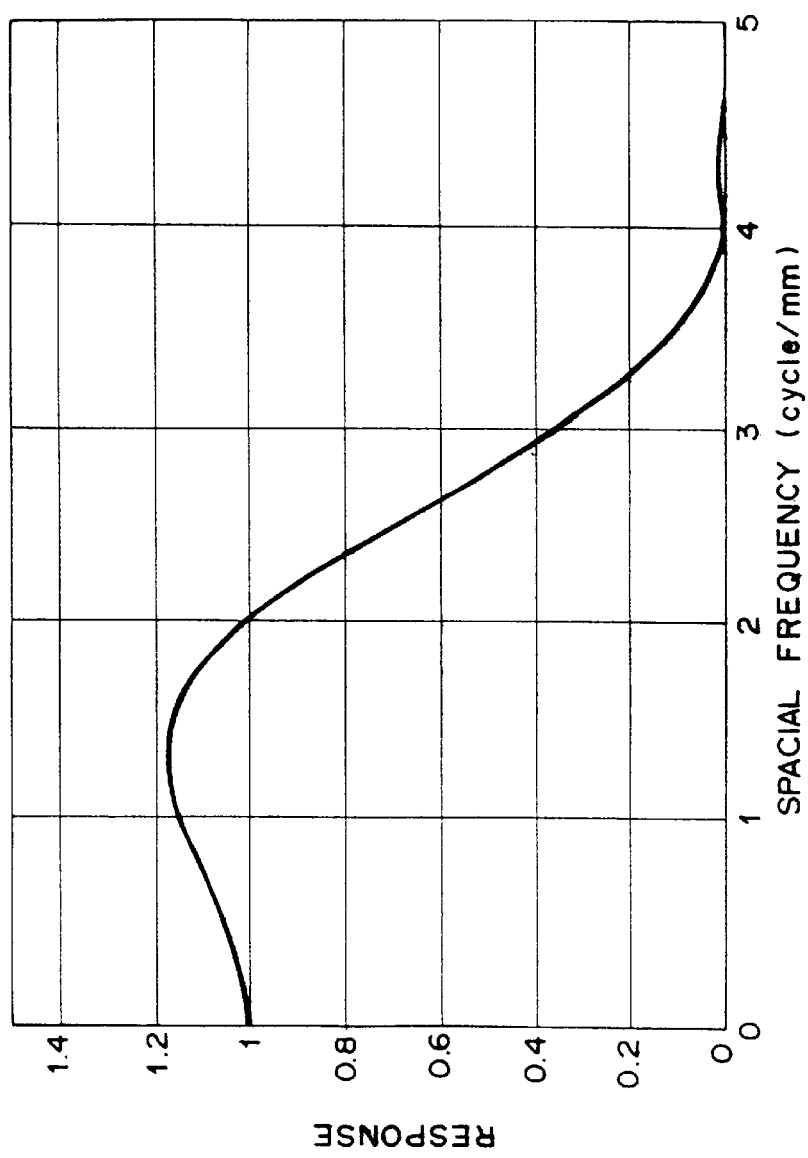
FIGS. 7 and 8 are graphs showing characteristics of conventional filters.
Figure 8:
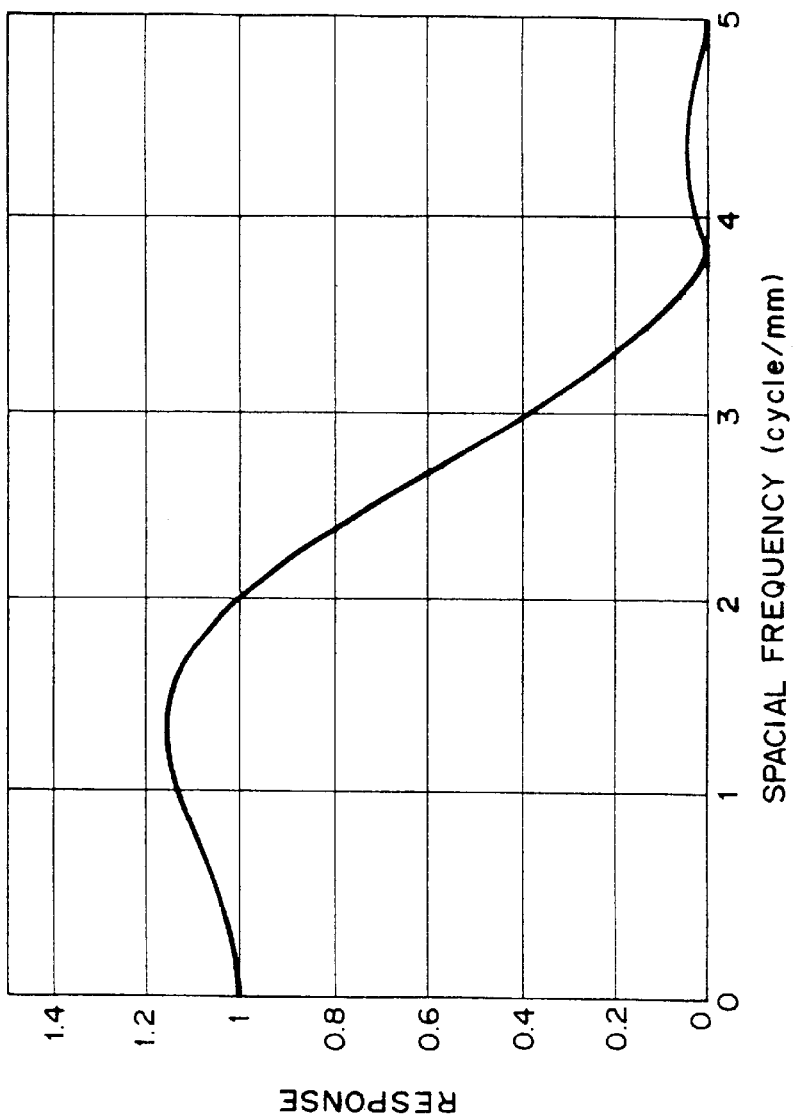

In the case where the reproduced image is reduced to ⅔, a filter F1 comprising 2 kinds of filters shown below is used. A characteristic of the filter F1 is shown by FIG. 6. The filtering processing using the filter F1 is carried out on the image data S1 by alternately applying the 2 kinds of filters below. −1, 0, 4, 0, −12, −7, 31, 66, 53, 9, −14, −6, 4, 2, 1 −1, 2, 4, −6, −14, 9, 53, 66, 31, −7, −12, 0, 4, 0, −1

The Nyquist frequency for the case of a ⅔ reduction image is 10/3 (approximately 3.3) cycles/mm. Therefore, the characteristic of the filter F1 is to reduce the response of the spacial frequency of equal to or more than 3.3 cycles/mm which is higher than the Nyquist frequency, as shown in FIG. 6. Therefore, even in the case where an image is reduced to ⅔, filtering processing using the filter F1 can reduce the response of spacial frequency of equal to or more than 3.3 cycles/mm to equal to or less than 5%, preferably to equal to or less than to 2%, and a stripe pattern to appear in the spacial frequency band of 3.4 cycles/mm or 4.0 cycles/mm can be suppressed.

In the above embodiment, a filter reducing the stripe pattern caused by the 3.4 line/mm pitch grid has been explained. However, the present invention is not limited to the above example, and any filter reducing a response of equal to or more than 97% of a spacial frequency corresponding to the pitch of the grid to be used to equal to or less than 5%, preferably to equal to or less than 2% can be adopted.

What is claimed is:

1. A moire eliminating filter to reduce a response of a spacial frequency component of a stripe pattern in image data obtained by reading an image including the stripe pattern corresponding to a grid of n line/mm pitch used at the time of photographing the image, the filter reducing a response of a spacial frequency component equal to or more than 97% of the spacial frequency component corresponding to the grid pitch to equal to or less than 5%.

2. An image processing method of carrying out filtering processing to reduce a response of a spatial frequency component of a stripe pattern on image data obtained by reading an image including the stripe pattern corresponding to a grid of n line/mm pitch used at the time of photographing the image, the image processing method carrying out the filtering processing by using a moire eliminating filter according to claim 1.

3. An image processing apparatus comprising filtering means for reducing a response of spatial frequency component of a stripe pattern in image data obtained by reading an image including the stripe pattern corresponding to a grid of n line/mm pitch used at the time of photographing the image, the filtering means carrying out filtering processing by using a moire eliminating filter according to claim 1.

4. The image processing apparatus of claim 1, wherein said moiré eliminating filter is a 15-degree filter having filter coefficients of −1, −1, 4, −3, −14, 0, 43, 68, 43, 0, −14, −3,4, 1, −1.

5. The image processing apparatus of claim 1, wherein said moiré eliminating filter comprises two 15-degree filters applied alternately applied to the image data.

6. The image processing apparatus of claim 5, wherein the two 15-degree filters have filter coefficients of −1, 0, 4, 0, −12, −7, 31, 66, 53, 9, −14, −6, 4, 2, 1 and −1, 2, 4, −6, 14, 9, 53, 66, 31, −7, −12, 0, 4, 0, −1 respectively.

7. The image processing apparatus of claim 1, wherein said filter reduces a response of the spatial frequency component corresponding to the grid lines to equal to or less than 2%.

8. The image processing apparatus according to claim 1, wherein said moiré eliminating filter comprises a set of filter coefficients, said set of coefficients including an odd number n of coefficients arranged in a sequence 1 to n, wherein the sequence of filter coefficients has a maximum value at a position (n+1)/2.

9. The image processing apparatus according to claim 8, wherein the set of filter coefficients is substantially symmetric in coefficient values about the maximum value at position (n+1)/2, wherein asymmetry in value in the sequence occurs at position ((n+1)/2)+x and ((n+1)/2)−x, wherein x<(n+1)/2.

10. The image processing apparatus according to claim 1, wherein the moiré eliminating filter comprises two filter coefficient sets, each coefficient filter set having an odd number n of coefficients arranged in a sequence 1 to n, and wherein each set of filter coefficients has a maximum value at a position (n+1)/2.

* * * * *